United States Patent [19]
Shlyankevich

[11] Patent Number: 5,523,087
[45] Date of Patent: Jun. 4, 1996

[54] PHARMACEUTICAL COMPOSITIONS FOR THE TREATMENT OF DIABETIC MALE SEXUAL DYSFUNCTION

[75] Inventor: Mark Shlyankevich, Watterbury, Conn.

[73] Assignee: Bio-Virus Research Incorporated, San Mateo, Calif.

[21] Appl. No.: 389,006

[22] Filed: Feb. 15, 1995

[51] Int. Cl.$^6$ .......................... A61K 35/78; A61K 31/56; A61K 31/35
[52] U.S. Cl. .................. 424/195.1; 514/182; 514/456
[58] Field of Search ..................... 514/456, 182; 424/195.1

[56] References Cited

U.S. PATENT DOCUMENTS

| | | | |
|---|---|---|---|
| 4,557,927 | 12/1985 | Miyake et al. | 424/48 |
| 5,059,603 | 10/1991 | Rubin | 514/264 |
| 5,118,671 | 6/1992 | Bombardelli et al. | 514/26 |
| 5,204,369 | 4/1993 | Vallee et al. | 514/456 |
| 5,358,720 | 10/1994 | Koppel et al. | 424/639 |

Primary Examiner—Raymond Henley, III
Attorney, Agent, or Firm—Herbert Dubno

[57] ABSTRACT

A pharmaceutical composition is disclosed for the treatment of diabetic male sexual dysfunction, which comprises:

(a) 45 to 60 parts by weight of one or more phytoestrogen compounds calculated as a free aglycon form of isoflavone;
(b) 0 to 400, preferably 200 to 300 parts by weight of phosphatidyl choline;
(c) 10 to 50 parts by weight of beta-sitosterol;
(d) 0 to 300, preferably 30 to 100 parts by weight of Damiana leaf dry extract;
(e) 0 to 15, preferably 1 to 3 parts by weight of Vitamin A;
(f) 0 to 250, preferably 20 to 100 parts by weight of Vitamin B1;
(g) 0 to 300, preferably 50 to 150 parts by weight of Vitamin B6;
(h) 0 to 100, preferably 10 to 70 parts by weight of Vitamin E;
(i) 0 to 300, preferably 50 to 200 parts by weight of calcium contained in a biologically acceptable calcium salt;
(j) 0 to 750, preferably 300 to 500 parts by weight of magnesium contained in a biologically acceptable magnesium salt; and
(k) 0 to 100, preferably 10 to 90 parts by weight of zinc contained in a biologically acceptable zinc salt; in admixture with a biologically acceptable inert carrier.

4 Claims, No Drawings

PHARMACEUTICAL COMPOSITIONS FOR THE TREATMENT OF DIABETIC MALE SEXUAL DYSFUNCTION

FIELD OF THE INVENTION

The present invention relates to a pharmaceutical composition for the treatment of diabetic male sexual dysfunction. More particularly, the invention relates to such pharmaceutical compositions that contain natural soybean phytoestrogens of the isoflavone group.

BACKGROUND OF THE INVENTION

The association between diabetes mellitus and erectile impotence is well known, and the frequency of these disorders ranges from 27 to 71%. In comparison to control subjects, diabetic patients show extensive behavioral decreases in sexual desire, arousal, activity and satisfaction. See Schiavi, R. C., Diabetologica, 36:745 to 751 (1993). The effect of glycemic control on the development of sexual problems is uncertain. In addition to the peripheral neurovascular pathology, the abnormal central nervous processes may also contribute to diabetic erectile dysfunction.

There have been reports that link diabetic erectile dysfunction to a transient gonadotropin deficiency. See Ishida, Y. et al, "Unusual Combination of Insulin-Dependent Diabetes Mellitus and Transient Pituitary Isolated Gonadotropin Deficiency", *Intern. Med.* (Japan), January 1994, 33(1) pp 27 to 30.

There have been several attempts made to treat diabetic male sexual dysfunction. According to Desvaux, P. et al, "Prostaglandin E1 in the Treatment of Erectile Insufficiency; Comparison of Efficacy and Tolerance Based on Different Etiologies", *J. Urol.* 100(1) pp 17 to 22 (1994). Some success has been obtained using a combination of papaverine and an alpha-blocker. Even more limited success has been achieved by administration of prostaglandin E1. However, as of yet there is no highly successful pharmaceutical for the treatment of this dysfunction.

OBJECT OF THE INVENTION

It is the object of this invention to provide a pharmaceutical composition and a method for the treatment of diabetic male sexual dysfunction.

SUMMARY OF THE INVENTION

This object is accomplished in accordance with the present invention which provides a composition for the treatment of diabetic male sexual dysfunction, which comprises:

(a) 45 to 60 parts by weight of one or more phytoestrogen compounds calculated as a free aglycon form of isoflavone;

(b) 0 to 400, preferably 200 to 300 parts by weight of phosphatidyl choline;

(c) 10 to 50 parts by weight of beta-sitosterol;

(d) 0 to 300, preferably 30 to 100 parts by weight of Damiana leaf dry extract;

(e) 0 to 15, preferably 1 to 3 parts by weight of Vitamin A;

(f) 0 to 250, preferably 20 to 100 parts by weight of Vitamin B1;

(g) 0 to 300, preferably 50 to 150 parts by weight of Vitamin B6;

(h) 0 to 100, preferably 10 to 70 parts by weight of Vitamin E;

(i) 0 to 300, preferably 50 to 200 parts by weight of calcium contained in a biologically acceptable calcium salt;

(j) 0 to 750, preferably 300 to 500 parts by weight of magnesium contained in a biologically acceptable magnesium salt; and (k) 0 to 100, preferably 10 to 90 parts by weight of zinc contained in a biologically acceptable zinc salt; in admixture with a biologically acceptable inert carrier.

The phytoestrogen is preferably soybean phytoestrogen which is an isoflavone selected from the group consisting of genistein, daidzein, their glycosides and mixtures thereof. The main soybean isoflavones are genistein and daidzein. In raw soybeans and soy flour they are conjugated with glucose (glycosides), and are named genistin and daidzin.

The free (aglycon) and conjugated forms of isoflavones have the following molecular weights, respectively:

Genistein 270,

Genistin 450

Daidzein 254,

Daidzin 434

In the present compositions the concentration of isoflavones is preferably about 30% by weight, and the principal form of the isoflavones will be as the abovementioned conjugates.

The breakdown of conjugated isoflavones concerning isoflavone and glucose are as follows:

45 mg of free isoflavones—80 mg of glycosides 60 mg of free isoflavones—105 mg of glycosides.

The preferred full weight of a pharmaceutical composition would be:

for 45 mg of free isoflavone—265 mg of composition for 65 mg of free isoflavone—350 mg of composition.

The full weight of the entire daily dose of the composition is preferably 1,000 to 1,500 mg, which should preferably be divided into two capsules, tablets or other forms that are easily orally administered. If preferred, this same total daily dosage may be divided into three or four doses.

In the new compositions for treating diabetic male sexual dysfunction besides the phytoestrogens, the following compounds are included as well:

Lecithin from soybean oil is important for nerve protection and repair.

Thiamine (Vitamin B1) is effective because its deficiency accompanies and intensifies neuropathy.

Vitamin A must be administered as retinol because diabetics cannot convert beta-carotene into Vitamin A.

Magnesium is very important in the treatment of neuropathy and diabetes. See Diabetes Care, 18(Suppl. 1): 83 to 85 (1995).

Beta-sinosterol (phytoestrol) from soybeans can improve the condition by means of decreasing cholesterol absorption.

Vitamin B6 in daily doses of about 150 mg and Damiana leaf are highly effective for the correction of male sexual dysfunction.

Vitamin E and zinc improve the functioning of the prostate gland and reproductive organ function.

The invention also relates to a method of treating diabetic male sexual dysfunction which comprises orally administering the abovementioned compositions to a male subject in need of said treatment. A normal daily dosage is from 500 to 1500 mg.

The following examples represent non-limiting preferred features characteristic of the instant invention:

EXAMPLE 1

The daily dose of ingredients is as follows:

| Constituents | Chemicals | Active Compound |
| --- | --- | --- |
| Soybean phytoestrogens | Genistein, Daidzein, and their glycosides | 45 mg (calculated as free aglycon form) |
| Lecithin from soybean | Phosphatidyl choline | 200 mg |
| Phytosterol from soybean | Beta-sitosterol (Sitosteryl-D-glucoside) | 10 mg |
| Damiama leaf | Damiana leaf dry extract | 30 mg |
| Vitamin A | Retinol palmitate | 1 mg |
| Vitamin B1 | Thiamine mononitrate | 50 mg |
| Vitamin B6 | Pyridoxine hydrochloride | 50 mg |
| Vitamin E | alpha-Tocopheryl acetate or succinate | 30 mg |
| Calcium | Calcium carbonate | 150 mg |
| Magnesium | Magnesium oxide | 300 mg |
| Zinc | Zinc sulfate | 80 mg |

EXAMPLE 2

The daily dose of ingredients is as follows:

| Constituents | Chemicals | Active Compound |
| --- | --- | --- |
| Soybean phytoestrogens | Genistein, Daidzein, and their glycosides | 60 mg (calculated as free aglycon form) |
| Lecithin from soybean | Phosphatidyl choline | 200 mg |
| Phytosterol from soybean | Beta-sitosterol (Sitosteryl-D-glucoside) | 50 mg |
| Damiama leaf | Damiana leaf dry extract | 100 mg |
| Vitamin A | Retinol palmitate | 3 mg |
| Vitamin B1 | Thiamine mononitrate | 50 mg |
| Vitamin B6 | Pyridoxine hydrochloride | 150 mg |
| Vitamin E | alpha-Tocopheryl acetate or succinate | 30 mg |
| Calcium | Calcium carbonate | 150 mg |
| Magnesium | Magnesium oxide | 500 mg |
| Zinc | Zinc sulfate | 80 mg |

What is claimed is:

1. A pharmaceutical composition for the treatment of diabetic male sexual dysfunction, which comprises:
   (a) 45 to 60 parts by weight of one or more phytoestrogen compounds calculated as a free aglycon form of isoflavone;
   (b) 0 to 400 parts by weight of phosphatidyl choline;
   (c) 10 to 50 parts by weight of beta-sitosterol;
   (d) 30 to 100 parts by weight of Damiana leaf dry extract;
   (e) 0 to 15 parts by weight of Vitamin A;
   (f) 0 to 250 parts by weight of Vitamin B1;
   (g) 0 to 300 parts by weight of Vitamin B6;
   (h) 0 to 100 parts by weight of Vitamin E;
   (i) 0 to 300 parts by weight of calcium contained in a biologically acceptable calcium salt;
   (j) 0 to 750 parts by weight of magnesium contained in a biologically acceptable magnesium salt; and
   (k) 0 to 100 parts by weight of zinc contained in a biologically acceptable zinc salt; in admixture with a biologically acceptable inert carrier.

2. The pharmaceutical composition for the treatment of diabetic male sexual dysfunction defined in claim 1 wherein the phytoestrogen is obtained from soy and is an isoflavone selected from the group consisting of genistein, daidzein, their glycosides, and mixtures thereof.

3. A method of treating diabetic male sexual dysfunction in a male mammalian subject which comprises the step of administering to said subject, a therapeutically effective amount of a pharmaceutical composition which comprises:
   (a) 45 to 60 parts by weight of one or more phytoestrogen compounds calculated as a free aglycon form of isoflavone;
   (b) 0 to 400 parts by weight of phosphatidyl choline;
   (c) 10 to 50 parts by weight of beta-sitosterol;
   (d) 0 to 300 parts by weight of Damiana leaf dry extract;
   (e) 0 to 15 parts by weight of Vitamin A;
   (f) 0 to 250 parts by weight of Vitamin B1;
   (g) 0 to 300 parts by weight of Vitamin B6;
   (h) 0 to 100 parts by weight of Vitamin E;
   (i) 0 to 300 parts by weight of calcium contained in a biologically acceptable calcium salt;
   (j) 0 to 750 parts by weight of magnesium contained in a biologically acceptable magnesium salt; and
   (k) 0 to 100 parts by weight of zinc contained in a biologically acceptable zinc salt; in admixture with a biologically acceptable inert carrier.

4. The method of treating male sexual dysfunction defined in claim 3 wherein the pharmaceutical composition contains 30 to 100 parts by weight of Damiana leaf dry extract.

* * * * *